United States Patent
Jo et al.

(10) Patent No.: US 11,357,576 B2
(45) Date of Patent: Jun. 14, 2022

(54) METHOD AND SYSTEM FOR AUGMENTED REALITY GUIDED SURGERY

(71) Applicant: DENTSPLY SIRONA Inc., York, PA (US)

(72) Inventors: Jeremy E. Jo, Somerville, MA (US); Jeffrey M. Ragazzini, Somerville, MA (US)

(73) Assignee: DENTSPLY SIRONA INC., York, PA (US)

( * ) Notice: Subject to any disclaimer, the term of this patent is extended or adjusted under 35 U.S.C. 154(b) by 136 days.

(21) Appl. No.: 16/110,511

(22) Filed: Aug. 23, 2018

(65) Prior Publication Data

US 2020/0008877 A1    Jan. 9, 2020

Related U.S. Application Data (60) Provisional application No. 62/694,127, filed on Jul. 5, 2018.

(51) Int. Cl.
| | |
|---|---|
| *A61B 34/20* | (2016.01) |
| *A61B 34/10* | (2016.01) |
| *A61B 6/14* | (2006.01) |
| *A61C 1/08* | (2006.01) |
| *A61C 13/00* | (2006.01) |

(52) U.S. Cl.
CPC ............. *A61B 34/20* (2016.02); *A61B 6/145* (2013.01); *A61B 34/10* (2016.02); *A61C 1/084* (2013.01); *A61C 13/0004* (2013.01); *A61B 2034/107* (2016.02)

(58) Field of Classification Search
None
See application file for complete search history.

(56) References Cited

U.S. PATENT DOCUMENTS

| | | | |
|---|---|---|---|
| 2002/0082498 A1 | 6/2002 | Wendt | |
| 2008/0199829 A1* | 8/2008 | Paley | A61B 5/1077 433/215 |

(Continued)

FOREIGN PATENT DOCUMENTS

WO    2015110859 A1    7/2015

OTHER PUBLICATIONS

Darko Katie, Patrick Spengler, Sebastian Bodenstedt, et al., "A system for context-aware intraoperative augmented reality in dental implant surgery", Jan. 2015, Springer, International Journal of Computer Assisted Radiology and Surgery, vol. 10, Issue 1, pp. 101-108.*

(Continued)

*Primary Examiner* — Robert Bader
(74) *Attorney, Agent, or Firm* — Dentsply Sirona Inc.

(57) ABSTRACT

A method and system for facilitating the placement of a dental implant device using augmented reality, and simultaneously capturing the result of the placement for subsequent planning procedures. By planning a desired dental implant location using one or more preoperative images of a patient and overlaying the planned dental implant location and the one or more preoperative images on the patient through virtual reality means, a clinician may be provided with an awareness of the positional relationship between the preoperative images and the planned implant position.

18 Claims, 4 Drawing Sheets

(56) References Cited

U.S. PATENT DOCUMENTS

| | | | | |
|---|---|---|---|---|
| 2012/0282567 A1* | 11/2012 | Nilsson | ............ | A61C 1/084 |
| | | | | 433/68 |
| 2016/0191887 A1 | 6/2016 | Casas | | |
| 2016/0324598 A1* | 11/2016 | Bothorel | ............ | A61B 34/20 |
| 2017/0202633 A1 | 7/2017 | Liu | | |
| 2018/0165818 A1* | 6/2018 | Tsai | ............ | A61B 6/4085 |
| 2018/0168780 A1* | 6/2018 | Kopelman | ............ | G09B 23/283 |
| 2018/0168781 A1 | 6/2018 | Kopelman | | |
| 2019/0046276 A1* | 2/2019 | Inglese | ............ | A61C 9/0046 |

OTHER PUBLICATIONS

Junchen Wang, Hideyuki Suenaga, Kazuto Hoshi, Liangjing Yang, Etsuko Kobayashi, Ichiro Sakuma, Hongen Liao, "Augmented Reality Navigation With Automatic Marker-Free Image Registration Using 3-D Image Overlay for Dental Surgery", Apr. 2014, IEEE, IEEE Transactions on Biomedical Engineering, vol. 61, No. 4, p. 1295-304.*
International Search Report; PCT/US2019/040220; Oct. 1, 2019 (completed); dated Oct. 12, 2019 (mailed).
Written Opinion of the International Searching Authority; PCT/US2019/040220; Oct. 1, 2019 (completed); dated Oct. 12, 2019 (mailed).
International Preliminary Reporton Patentability; PCT/US2019/040220; Oct. 1, 2019 (completed); dated Oct. 12, 2019 (mailed).

* cited by examiner

METHOD AND SYSTEM FOR AUGMENTED REALITY GUIDED SURGERY

FIELD OF THE INVENTION

The present application relates generally to a method and a system for image guided surgery and, more particularly, to a method and a system for the guided placement of a dental implant during a dental procedure and using augmented reality, and simultaneously capturing the result of the placement for subsequent planning procedures.

BACKGROUND OF THE INVENTION

Various options exist for treating dental defects such as by the use of restorations as well as the placement of dental implants using physical guides/sleeves and restorations to restore tooth functions. Another option is the use of robotic surgery to place dental implants.

Clinicians may digitally visualize and manipulate a location where a dental implant may be located relative to bone and nerve tissue using a computer and a digital image or scan, such as CBCT or x-ray. However, achieving the ideal implant location may require assistance in the form of a physical guide or robotic surgery. Physical guides require manufacturing and shipping time and robotic surgery is expensive.

The placement of dental implants using physical guides typically involve a patient and a clinician waiting multiple days between Cone Beam Computed Tomography (CBCT) scanning and an implant placement procedure so that the physical guide may be designed/manufactured and/or shipped. This may require separate appointments for scanning and implant placement which may be time consuming and expensive.

With existing implant placement techniques, an error of final implant location may be between 200-1000 microns relative to a planned implant location. The variability allowable for accurate restoration design is much smaller, requiring precisions of <100 microns. Because the implant cannot be placed accurately enough for reliable restoration design, an impression may be taken after the implant placement as an input to a restoration design process. This impression may provide a digital representation of the implant's location relative to neighboring dentition with enough accuracy to design and produce a restoration. However the procedure may require additional scanning equipment during the surgery, the use of intra-oral scan flags or traditional impression components/materials, and possibly an additional patient visit to the clinician for digital or physical impression-taking. By capturing the geometric details/results of the guided implant placement, an additional impression may not be required for restoration design, eliminating the need for intra-oral scan flags, intra-oral scanning during or after implant placement, or an additional appointment for impression taking.

US Patent Application No. 2017202633 discloses an imaging and display system for guiding medical interventions comprising a wearable display for viewing by a user wherein the display presents a composite, or combined image that includes pre-operative surgical navigation images, intraoperative images, and in-vivo microscopy images or sensing data. A probe, such as a microscopy probe or a sensing probe, may be used to acquire in-vivo imaging/sensing data from the patient and the intra-operative and in-vivo images may be acquired using tracking and registration techniques to align them with the pre-operative image and the patient to form a composite image for display.

US Patent Application No. 20020082498 discloses a method for image-guided surgery comprising capturing 3-dimensional (3D) volume data of a portion of a patient, processing the volume data so as to provide a graphical representation of the data, capturing a stereoscopic video view of a scene including a portion of said patient, rendering the graphical representation and the stereoscopic video view in a blended manner so as to provide a stereoscopic augmented image, and displaying said stereoscopic augmented image in a video-see-through display.

US Patent Application Publication No. 20160191887 describes a real-time surgery navigation method and apparatus for displaying an augmented view of a patient from a static or dynamic viewpoint of a surgeon. A surface image, a graphical representation the internal anatomic structure of the patient processed from preoperative or intraoperative images, and a computer geometrically registering both images may be used. Responsive to geometrically registering the images, a head mounted display may present to a surgeon an augmented view of the patient.

SUMMARY OF THE INVENTION

Existing limitations associated with the foregoing, as well as other limitations, can be overcome by a method and a system for the guided placement of a dental implant during a dental procedure and using augmented reality, and simultaneously capturing the result of the placement for subsequent planning procedures.

In an aspect herein, the present invention may provide a method utilizing augmented visualization, the method comprising: obtaining one or more preoperative images of a patient; geometrically registering the one or more preoperative images together based on common features or reference points in the one or more preoperative images; providing a treatment plan including a planned implant location; overlaying the geometrically registered preoperative images and/or the planned implant location on the patient such that they appear directly superimposed on target regions of the patient; and providing navigational instructions for creating a drilling hole and/or inserting an implant based on a positional relationship between the overlaid geometrically registered preoperative images and the planned implant location.

In another aspect herein, the method may further comprise one or more of the steps (i) further comprising determining a final location of the implant, and designing a restoration based on the final implant location, (ii) further comprising determining the final location of the implant is based on (a) a geometry data of the handpiece, components of the handpiece and/or implant and/or (b) postoperative images of the treatment region, (iii) further comprising determining the final location of the implant by (a) tracking a clinical environment of the patient; (b) tracking a handpiece location relative to the clinical environment; (c) tracking a drill location relative to the handpiece location; (d) obtaining a drill location relative to the clinical environment; and (e) obtaining dimensions of an implant driver used to drive the implant into the final location, (iv) wherein the preoperative images include X-ray scan data, intra-oral scan data and/or facial scan data. (v) wherein the geometric registration is manual or autonomous (vi) wherein the common features or reference points include predetermined markers, bite plane and/or dental anatomical features, (vii) wherein information about the planned implant location includes an optimal bore hole for the implant, (viii) further comprising updating positions of the geometrically registered preoperative images and/or the planned implant location using a tracking means, (ix) wherein the navigational instructions are in visual/digital, auditory, and/or haptic forms.

In another aspect, a system may be provided, the system utilizing augmented visualization, the system comprising: at least one processor configured to; obtain one or more preoperative images of a patient; geometrically register the one or more preoperative images together based on common features or reference points in the one or more preoperative images; provide a treatment plan including a planned implant location; overlay the geometrically registered preoperative images and/or the planned implant location on the patient such that they appear directly superimposed on target regions of the patient; and provide navigational instructions for creating a drilling hole and/or inserting an implant based on a positional relationship between the overlaid geometrically registered preoperative images and the planned implant location. In another aspect, the system may include one or more of the configurations (i) the system further comprising a display device configured to receive images for said overlay, (ii) the system further comprising tracking means configured to offer real-time position data for a precise location and orientation of images and objects in a common coordinate system, (iii) the system wherein the tracking means is sensor based and/or vision based. (iv) the system wherein the processor is further configured to: determine a final location of the implant, and design a restoration based on the final implant location, (v) the system wherein the processor is further configured to determine the final location of the implant based on (a) a geometry data of the handpiece, components of the handpiece and/or implant and/or (b) postoperative images of the treatment region, (vi) the system wherein the processor is further configured to determine the final location of the implant by (a) tracking a clinical environment of the patient; (b) tracking a handpiece location relative to the clinical environment; (c) tracking a drill location relative to the handpiece location; (d) obtaining a drill location relative to the clinical environment; and (e) obtaining dimensions of an implant driver used to drive the implant into the final location, (vii) the system wherein the preoperative images include X-ray scan data, intra-oral scan data and/or facial scan data, (viii) the system wherein the geometric registration is manual or autonomous, (ix) the system wherein the common features or reference points include predetermined markers, bite plane and/or dental anatomical features, (x) the system wherein information about the planned implant location includes an optimal bore hole for the implant, (xi) the system wherein the processor is further configured to provide the navigational instructions in visual/digital, auditory and/or haptic forms.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein and wherein.

Different ones of the figures may have at least some reference numerals that may be the same in order to identify the same components, although a detailed description of each such component may not be provided below with respect to each Figure.

DETAILED DESCRIPTION OF THE INVENTION

In accordance with example aspects described herein, a method and system may be provided for using a plurality of digital and/or physical data inputs to provide and facilitate the placement of a dental implant device 4 using an augmented reality portal, and simultaneously allowing for capturing the result of the placement for subsequent planning procedures such as restoration design. By planning a desired dental implant location 32 using one or more preoperative images of a patient and overlaying the planned dental implant location/planned surgical site 32 and the one or more preoperative images on the patient through virtual reality means, a clinician may be provided with an awareness of the positional relationship between the preoperative images and the planned surgical site 32 and may therefore be guided through an implant drilling procedure. Said overlay may mean but may not be limited to (i) providing images on the display such that they appear as if they were located directly on the patient when viewed through the display and/or (ii) projecting images directly onto target sites 14a of the patient using a projector. Moreover, by recording or capturing a final location of the implant 34 (the final implant location 34 including any deviations from the planned implant location 32) after surgery and combining the final implant location 34 information with reference scans of a patient, a dental restoration may be designed based on the final implant location 34, eliminating the need to for a dental impression typically taken prior to restoration design.

System for Augmented Reality Guided Surgery

Figure 1:
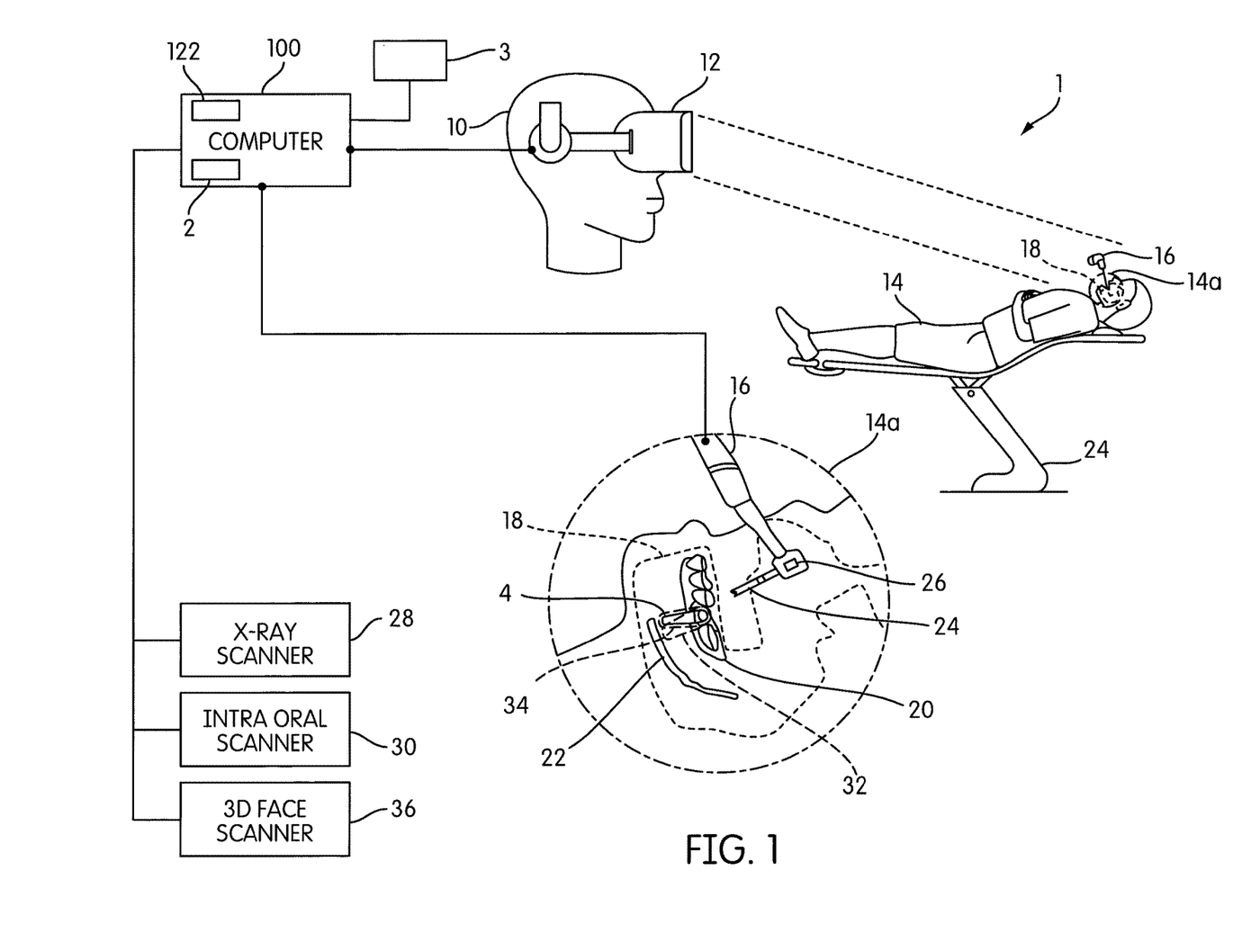
FIG. 1 is a diagram illustrating a system according to an embodiment of the present invention.

FIG. 1 illustrates a system 1 comprising a display device 12 such as head mounted augmented reality glasses, an HUD display or a stereoscopic display capable of receiving stereoscopic video images otherwise display device 12 that may be used for overlaying an image such as a CBCT or MRI image 18, intra oral image 20, facial image (not shown) or otherwise image on a patient 14 or on a stereoscopic video of the patient 14 as the patient 14 is seated in a treatment chair 24. CBCT or MRI data may show existing dental anatomy, including dentition, bone and nerve geometries, intra-oral scan data may show soft tissue and topographical surface/dentition geometry, and a 3D Face Scan and/or conventional photograph of the face may show the location of the mouth/teeth relative to other facial features such as the nose or surgical marks.

The display device 12 may be connected to or form part of a computer system 100. The computer system 100 (also shown in FIG. 2) may include a tracking means 2 and a processor 122. The tracking means 2 may alternatively form at least part of any of the devices, components, and/or systems discussed herein. The tracking means 2 may be electrically connected to a processor 122 and may offer real-time location data for a precise location and orientation of images and objects in a common coordinate system. In an exemplary embodiment herein, the tracking means may be sensor based (e.g. as embedded sensors 26 or markers in a handpiece 16, such as pressure, touch, proximity, ultrasonic, infrared, rotational, and gyroscopic sensors and accelerometers, to track the position of the handpiece or rotation cycles of a drill 24 in the handpiece 16, as gyroscopes and/or accelerometers to track the movement of the patient 14 and/or the clinician 10, and the like). In another embodiment, the tracking means may be vision based, for example as cameras for visual tracking of (i) the patient 14 or (ii) markers (not shown) on the patient 14, In yet another embodiment, the tracking means may be a fusion of sensor based and vision based tracking means. Moreover a wireless protocol may be used to transmit known marker locations for tracking.

The system may further comprise an X-ray Scanner 28 (CBCT/MRI Scanner) for obtaining preoperative CBCT/MRI scans of a treatment site, an intra oral scanner 30 for obtaining preoperative 3D images of the patient's mouth and/or a 3D Face Scanner 36 for obtaining a 3D scan of the face. A camera system 3 such as a 3D optical tracking system and/or stereoscopic camera system may be included in the computer system and may form or be a part of the tracking means 2. Alternatively, the camera system 3 may be embedded in the display device 12 of the clinician 10 or may be a part of the tracking means 2.

The processor 122 may be configured to receive CTCB/MRI data 18, intraoral images 20 and/or facial scan and geometrically register them together to be overlaid onto the patient 14 through for example see-through Augmented Reality Glasses/HUD display or onto a stereoscopic video of the patient using e.g. through a head mounted stereoscopic display. A treatment plan, including a planned implant location 32 (the planned implant location optionally including a planned/desired drill depth) may also be geometrically registered with the CBCT/MRI 18 and intra-oral 20 images and/or 2D/3D facial scan and overlaid onto the treatment site 14a. In another embodiment, the treatment plan/planned implant location 32 may optionally be overlaid on the treatment site 14a after a request is received from the clinician and/or after the preoperative images have been separately registered together. In an embodiment herein, the geometrically registered images may be adjusted by the clinician 10 through a user interface 126 of the computer system 100 (such as a gesture recognition system and/or a voice recognition system or the like) before or during the implant drilling procedure discussed hereinafter.

To execute a procedure, the processor 122 may load appropriate instructions, as stored on a memory device and may then execute the loaded instructions. Overlaying of the CBCT/MRI and/or intra-oral images on the patient 14 through the display may be performed dynamically and in real time and may be achieved by the processor 122 working in tandem with the tracking means 2 wherein changes in position of (i) the patient 14 and (ii) the clinician 10, captured by the tracking means 2, may be translated into corresponding changes in positions of the overlaid images such that the overlaid images appear directly superimposed on target regions/sites 14a (e.g. buccal cavity) of the patient 14. Herein, responsive to the clinician 10 moving his head around to view the spatial relationship between the internal structures of the patient shown in the overlaid images, from varying positions, the processor may be configured to provide the registration between the CBCT data 18 and the intra-oral data 20, giving the clinician 10 direct and precise access to the patient specific preoperative image information related to the implant drilling procedure. Instructions for said implant drilling procedure may be controlled by the processor 122 and optionally shown on the display 12 and may include but may not be limited to (i) activating visual/digital or auditory cues when the drill 24 of the handpiece 16 deviates from the overlaid planned implant location 32, (ii) deactivating the handpiece 16 when the drill 24 of the handpiece 16 deviates from the overlaid planned implant location 32, (iii) showing the distance of the drill 24 from important nerves 22 (e.g. alveolar nerve) and areas of optimal bone quality and quantity for implant placement in the display, said distance being computed from the preoperative images and motion data (e.g. drill rotation data) from the tracking means 2. The result of the implant drilling procedure may be captured by the tracking means 2 and/or camera system 3 as postoperative images for further design as described in the methods discussed hereinafter.

Computer System for Augmented Reality Guided Surgery

Having described a system 1 for facilitating the placement of a dental implant device 4 using an augmented reality portal, and simultaneously capturing the results for subsequent planning procedures, reference will now be made to FIG. 2, which shows a block diagram of a computer system 100 that may be employed in accordance with at least some of the example embodiments herein. Although various embodiments may be described herein in terms of this exemplary computer system 100, after reading this description, it may become apparent to a person skilled in the relevant art(s) how to implement the disclosure using other computer systems and/or architectures.

In one example embodiment herein, the computer system 100 may include at least one computer processor 122 and may include a tracking means 2, user interface 126 and input unit 130. The input unit 130 may be used by a user of the computer system 100 along with a display unit 128 such as a monitor to send information to the computer processor 122. In one exemplary embodiment herein, the input unit 130 is a finger or stylus to be used on a touchscreen interface 21. The input unit 130 may alternatively be a gesture/voice recognition device, a trackball, a mouse or other input device such as a keyboard or stylus. In one example, the display unit 128, the input unit 130, and the computer processor 122 may collectively form a user interface 126.

The computer processor 122 may include, for example, a central processing unit, a multiple processing unit, an application-specific integrated circuit ("ASIC"), a field programmable gate array ("FPGA"), or the like. The processor 122 may be connected to a communication infrastructure 124 (e.g., a communications bus, or a network). In an embodiment herein, the processor 122 may receive a request that a registration of the preoperative images is needed or a treatment plan for an implant drilling procedure is needed and may obtain instructions concerning the request from a memory of the modeling system 152 and/or a from one or more storage units of the computer system 100. The processor 122 may then load the instructions and execute the loaded instructions such as overlaying the geometrically registered images on the treatment site through the display 12 of the clinician 10. In an alternative embodiment, the computer system may use projection based augmented reality systems wherein, for example, a projector and depth sensors, along with the tracking means 2 and/or markers on the patient 14 (e.g. hidden markers) may project the preoperative images as well as the planned treatment location directly onto target sites 14a (e.g. buccal cavity) of the patient. Herein, a display 12 such as augmented reality glasses may not be needed.

The user interface (or other output interface) 126 may forward video graphics, text, and other data from the communication infrastructure 124 (or from a frame buffer (not shown)) for display on the display unit 128 (which, in one example embodiment, may form or be included in the display 12 of the clinician). For example, the user interface 126 may include a video card with a graphics processing unit.

One or more steps for overlaying the images may be stored on a non-transitory storage device in the form of computer-readable program instructions. To execute a procedure, the processor 122 loads the appropriate instructions, as stored on a storage device, into memory and then executes the loaded instructions.

Figure 2:
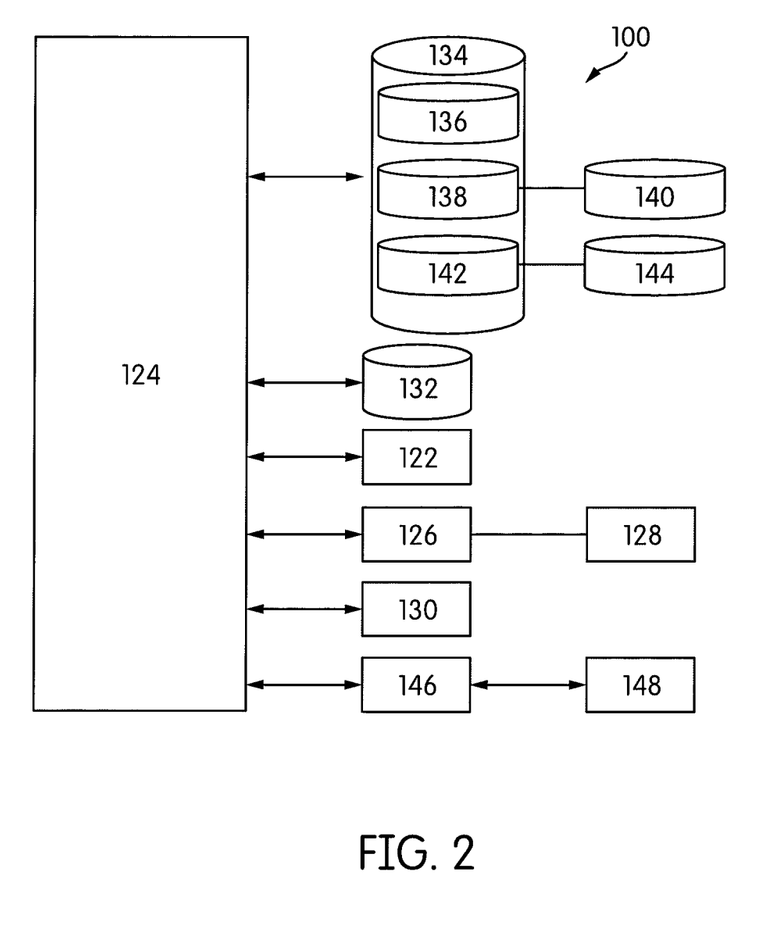
FIG. 2 illustrates a block diagram of an exemplary computer system according to an embodiment of the present invention.

The computer system 100 of FIG. 2 may further comprise a main memory 132, which may be a random access memory ("RAM") and also may include a secondary memory 134. The secondary memory 134 may include, for example, a hard disk drive 136 and/or a removable-storage drive 138 (e.g., a floppy disk drive, a magnetic tape drive, an optical disk drive, a flash memory drive, and the like). The removable-storage drive 138 may read from and/or write to a removable storage unit 140 in a well-known manner. The removable storage unit 140 may be, for example, a floppy disk, a magnetic tape, an optical disk, a flash memory device, and the like, which may be written to and read from by the removable-storage drive 138. The removable storage unit 140 may include a non-transitory computer-readable storage medium storing computer-executable software instructions and/or data.

In further alternative embodiments, the secondary memory 134 may include other computer-readable media storing computer-executable programs or other instructions to be loaded into the computer system 100. Such devices may include a removable storage unit 144 and an interface 142 (e.g., a program cartridge and a cartridge interface); a removable memory chip (e.g., an erasable programmable read-only memory ("EPROM") or a programmable read-only memory ("PROM")) and an associated memory socket; and other removable storage units 144 and interfaces 142 that allow software and data to be transferred from the removable storage unit 144 to other parts of the computer system 100.

The computer system 100 also may include a communications interface 146 that enables software and data to be transferred between the computer system 100 and external devices. Such an interface may include a modem, a network interface (e.g., an Ethernet card or an IEEE 802.11 wireless LAN interface), a communications port (e.g., a Universal Serial Bus ("USB") port or a FireWire® port), a Personal Computer Memory Card International Association ("PCM-CIA") interface, Bluetooth®, and the like. Software and data transferred via the communications interface 146 may be in the form of signals, which may be electronic, electromagnetic, optical or another type of signal that may be capable of being transmitted and/or received by the communications interface 146. Signals may be provided to the communications interface 146 via a communications path 148 (e.g., a channel). The communications path 148 carries signals and may be implemented using wire or cable, fiber optics, a telephone line, a cellular link, a radio-frequency ("RF") link, or the like. The communications interface 146 may be used to transfer software or data or other information between the computer system 100 and a remote server or cloud-based storage (not shown).

One or more computer programs or computer control logic may be stored in the main memory 132 and/or the secondary memory 134. The computer programs may also be received via the communications interface 146. The computer programs may include computer-executable instructions which, when executed by the computer processor 122, cause the computer system 100 to perform the methods as described hereinafter.

In another embodiment, the software may be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, causes the computer system 100, and more generally the system for augmented reality guided surgery, to perform all or some of the some of the methods described herein.

Implementation of other hardware arrangement so as to perform the functions described herein will be apparent to persons skilled in the relevant art(s) in view of this description.

Method for Augmented Reality Guided Surgery.

Figure 3:
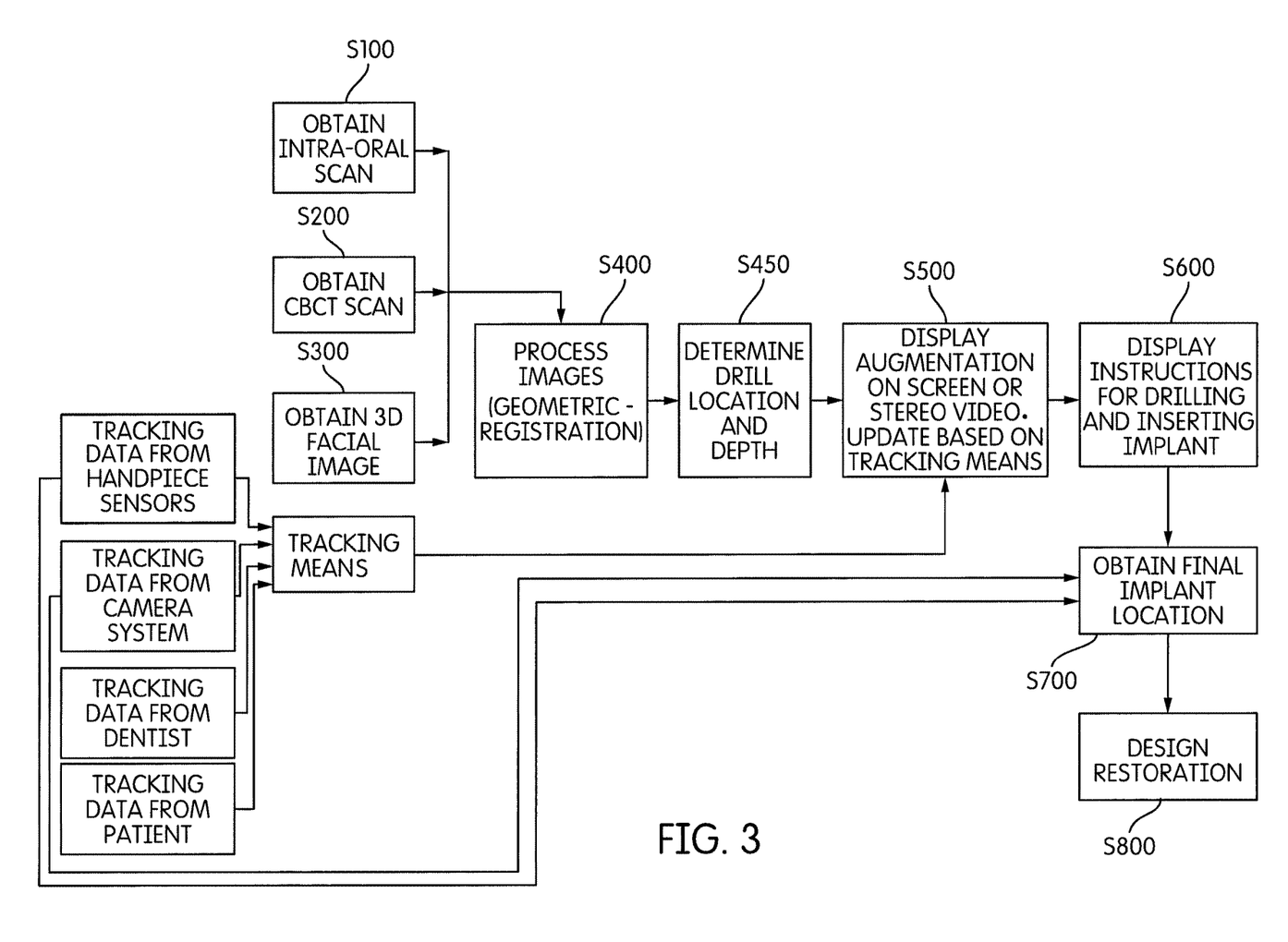
FIG. 3 is a diagram showing a method according to an embodiment of the present invention.
Figure 4:
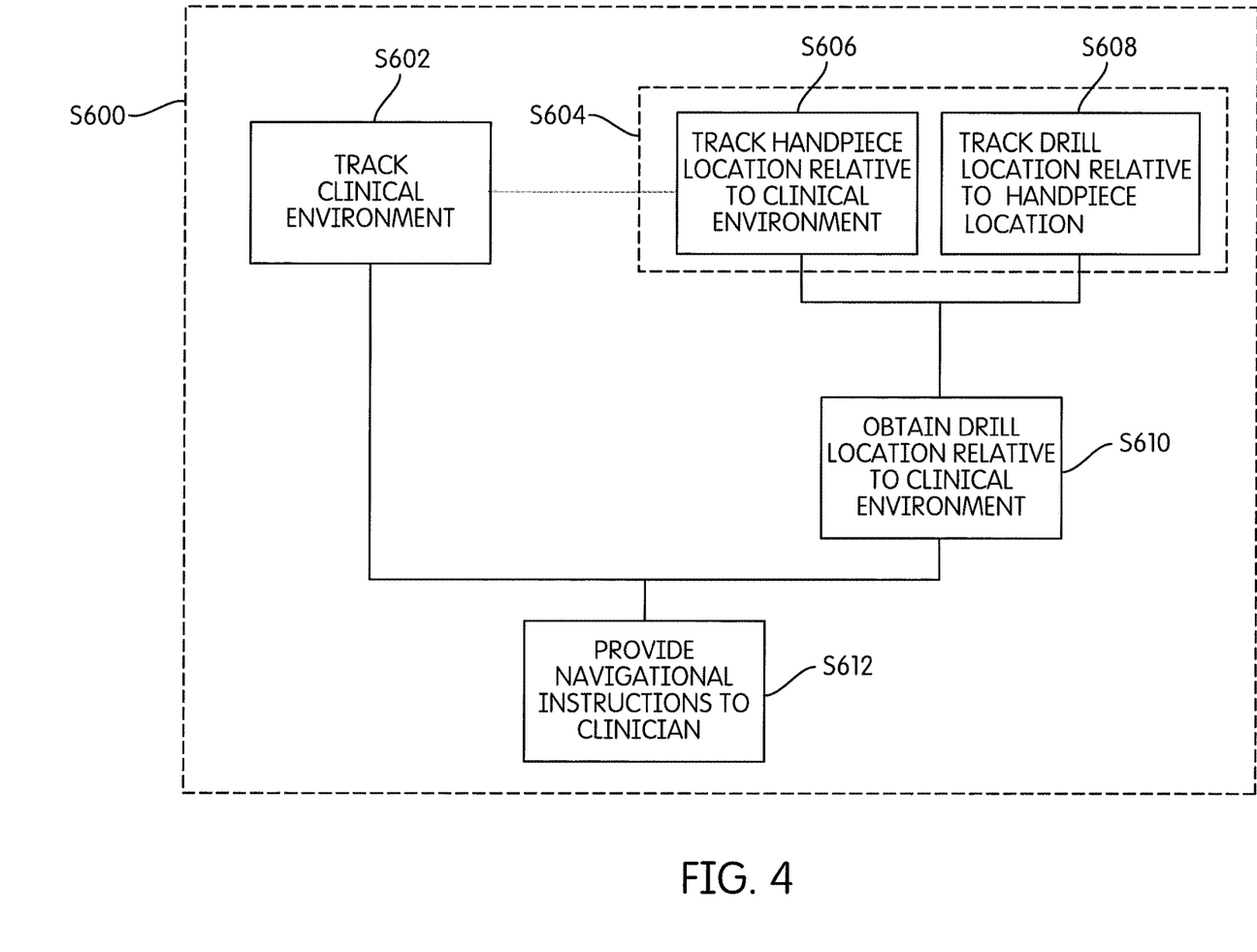
FIG. 4 illustrates another diagram showing another method according to an embodiment of the present invention.

Having described the computer system 100 of FIG. 2, the methods for augmented reality guided surgery will now be further described in conjunction with FIGS. 3-4 which show methods of facilitating the placement of a dental implant device 4 using augmented reality, and simultaneously capturing the result of the placement for subsequent planning procedures such as restoration design.

The method may include using a plurality of digital and physical data inputs to provide and facilitate the placement of the dental implant 4.

A primary preoperative image may be obtained in Step S100 of FIG. 3. The image may be an x-ray scan 18 of a patient's 14 specific dental anatomy or target site 14a. Captured within this scan may be data on bone density, bone quality, bone porosity, location of relevant nerves 22, anatomy of neighboring teeth, and other landmarks that are necessary to determine the ideal location (planned implant position 32) for a dental implant 4. This data may be captured using volumetric scanning methods such as a CBCT, MRI, and/or 2-D x-ray imaging.

A secondary preoperative image may be obtained in Step S200. The image may be optional and may include a set of reference surfaces, such as an intra-oral scan 20 of the teeth and gums, which may be geometrically registered to the x-ray 18.

In an embodiment, yet another preoperative image (a tertiary input) may be obtained in Step S300. The image may be a two- or three-dimensional facial image, which may be geometrically registered to both the primary and the secondary inputs in a processing step, Step S400. The image may be taken with reference points as necessary, wherein recognition of 3D objects (e.g. eyes, nose, chin etc.) or 2D patterns (e.g. marks from surgical skin marker) by tracking means 2 or camera system 3 may be used as additional navigational waypoints during surgery. The geometric registration may be achieved manually or autonomously by detecting common features in different medical image types (e.g. the approximate bite plane in CBCT and intra-oral scan data, arch articulation, gingival/dental anatomical features, the partition between lips in a facial 2D or 3D image and the like), stitching the images together using the detected features, and/or iteratively refining the registration by best-fitting algorithms (such as iterative closest point algorithms). Moreover, predetermined reference markers may be used on the patient (such as on the skin or in the mouth) as auxiliary calibration reference points for the geometric registration. A resulting fully-registered "stack" of medical images/preoperative images may be used as a reference model for further planning and execution of the implant placement procedure.

The processor 122 may be configured to provide a patient specific implant placement protocol based on the geometric registration. Herein the preoperative images may be correlated and an optimal drilling hole for the dental implant 4 at a planned implant location 32 may be determined, Step S450, based on information contained (e.g. position of the alveolar nerve, bone density, relative location of surfaces of the neighboring teeth etc.) in the x-ray scan 18 and/or the intraoral scan 20. Other information that may be needed for the determination may include the implant design/geometry, implant location (height, angulation, rotation), and surgical procedure details such as the ideal incision site and drilling protocol. One or more of the information may be pre-known or provided to the processor 122. Moreover, the processor 122 may utilize any of the devices described herein, e.g. camera system 3, embedded sensors 26 etc., to determine one or more of the information needed for said determination. In an alternative embodiment, the clinician 10 may alter or determine the planned implant location 32.

During the surgery process, the processor may be configured to display the geometrically registered images on the display 12, Step S500. From the clinicians view, the images may be overlaid onto the target site 14a. This overlay may be updated using the tracking means such that the images appear directly superimposed on target sites of the patient even as the patient moves. This may allow the clinician 10 to navigate in real time and pilot the dental implant 4 using the planned implant location 32. This may also remove the need for any physical guidance device or the usage of registration flags during surgery like those commonly used in navigated surgery procedures.

In an exemplary embodiment, to increase the accuracy of the drill, embedded sensors 26 may be integrated into the handpiece 16 to translate an orientation of the implant relative to the drill 24 into an orientation of the implant relative to the dental environment for tool navigation as described in more detail hereinafter. Additionally, visual markings and features that may be detectable by camera system 3 may be integrated into the handpiece 16 to measure an absolute orientation of the handpiece 16 relative to the patient's dentition. To confirm the location of the dental implant after insertion, predetermined features may be included on occlusal surface of a healing abutment (not shown) for the dental implant 4. Using the augmented reality camera, the final location 34 of the final implant as opposed to the planned location 32 may be obtained for the design of a restoration.

Navigational instructions for the clinician 10 for (a) creating a drilling hole to insert the dental implant 4 and (b) inserting the implant may be obtained as shown in Step S600 and in FIG. 4 by: (i) Tracking the clinical environment (patient's head/face/mouth etc.) in Step S602 using, for example, the camera system 3 (e.g. 3D optical tracking system) and facial landmarks (such as nose, mouth etc.) and/or predetermined markers (such as ink marks on the soft tissue of the buccal cavity, markers attached to the teeth and the like). (ii) Tracking the handpiece 26, and drill 24 as shown in Step S604, wherein the location of the handpiece 16 relative to the patient 14 may be tracked in Step S606 and the location of the drill 24 relative to the handpiece may be obtained in Step S608 and combined with the location of the handpiece relative to the clinical environment to obtain the location of the drill 24 relative to the clinical environment, Step S610. (iii) Providing instructions for navigating the drill 24 and placing the implant 4 (Step S612). Herein once the drill 24 locations are known relative to the clinical environment, navigational recommendations may be provided to the user in one or more forms including (a). visual form wherein for example red-yellow-green lights, colored lights or otherwise lights indicating accuracy of drilling depth (as compared to depth of the implant at the planned implant location 32) may be displayed on the display 12, (b). auditory form wherein for example verbal queues or other audible sounds are activated indicating where to move the drill 24, when to start/stop drilling), (c) haptic form wherein for example an intensity of vibration of vibrating element (not shown) is increased or decreased as the tool approaches a predetermined drill depth. In an embodiment herein, the handpiece 16 may be deactivated if the location of the drilling deviates from the planned implant location 32 by a predetermined amount (e.g. 0.5-2 mm) or if the drill is close to a nerve 22 that should not be damaged.

After drilling, the implant 4 may be inserted into the drilled hole by attaching the implant 4 to an implant driver tool, attaching the implant driver to the handpiece, and drilling the implant 4 into place. From Step S610, the location of the implant relative to the handpiece may be determined by the processor using the length/dimensions of the implant driver. The location of the handpiece relative to the clinical environment is also known by ongoing tracking of the patient and handpiece. Furthermore, the rotational orientation of the implant's internal mating geometry correlates to the rotational orientation of the implant driver by the driver's implant-interface geometry. Likewise, the rotational position of the implant driver may be monitored and recorded with for example a rotational potentiometer in the handpiece 16. Combining the resulting clinical data, handpiece/component geometry data, driver geometry data, and/or postoperative images from camera system 3 provides information for defining the final implant location 34, Step S700 (FIG. 3), within the patient's dentition. This location data, combined with the initial intraoral scan data 20 of neighboring dentition and soft tissue, may be used as inputs for designing a dental restoration such as final or temporary abutments, crowns, healing abutments, bridges and any other devices that may require knowledge of a location of an implant in order to correlate it to the surrounding dental anatomy for restorative or cosmetic purposes. (Step S800). Herein a physical impression may no longer be needed to determine the final implant location as would be required otherwise and the time spent in a clinician's office may be reduced.

In yet another embodiment, the geometrically registered images may not be overlaid on the patient 14. Instead, the clinician 10 may insert an implant 4 through, for example, conventional means and a final location of the inserted implant 4 may be obtained using tracking means 2/camera system 3 wherein for example embedded sensors 26 in the handpiece 16 and/or postoperative images may be employed. Having knowledge of the final position of the implant, planning/design processes such as the design of a restoration may be achieved without the need to take a physical impression.

In view of the foregoing description, it may be appreciated that the example embodiments described herein provide a method and system for facilitating the placement of a dental implant device 4 using augmented reality, and simultaneously capturing the result of the placement for subsequent planning procedures such as restoration design.

Unless otherwise defined, all technical and scientific terms used herein have the same meaning as commonly understood by one of ordinary skill in the art to which this invention belongs. Although methods and materials similar to or equivalent to those described herein may be used in the practice or testing of the disclosure, suitable methods and materials are described above. All publications, patent applications, patents, and other references mentioned herein are incorporated by reference in their entirety to the extent allowed by applicable law and regulations. The disclosure may be embodied in other specific forms without departing from the spirit or essential attributes thereof, and it may therefore be desired that the present embodiment be considered in all respects as illustrative and not restrictive. Any headings utilized within the description are for convenience only and have no legal or limiting effect.

What is claimed is:

1. A method utilizing augmented visualization, the method comprising;
   obtaining one or more preoperative images of a patient;
   responsive to the one or more preoperative images being a plurality of preoperative images, geometrically registering the plurality of preoperative images together based on common features or reference points in the plurality of preoperative images;
   providing a treatment plan including a planned implant location;
   overlaying the (i) one preoperative image or geometrically registered preoperative images and the (ii) planned implant location on the patient such that they appear directly superimposed on target regions of the patient, the overlaying defining a positional relationship between the one preoperative image or geometrically, registered preoperative images and the planned implant location; and
   continuously updating, using a tracking device, the overlaid one preoperative image or geometrically registered preoperative images and the planned implant location in real time such that they appear directly superimposed on said target regions of the patient:
   providing navigational instructions for creating a drilling hole based on (a) said positional relationship and (b) data tracking a clinical environment of the patient, data tracking a handpiece location relative to the clinical environment of the patient and data tracking movements of the drill based on drill geometry data; and
   providing navigational instructions for, responsive to creating the drilling hole, placing an implant into said drilling hole based on (a) said positional relationship and (c) data tacking clinical environment of the patient, data tracking a handpiece location relative to the clinical environment of the patient and data tracking movements of an implant driver based on driver geometry data
   further comprising:
   responsive to placing the implant into said drilling hole, determining a final implant location, by capturing geometric information about the placed implant, based on d) a geometry data of the handpiece, components of the handpiece and/or implant said capturing being devoid of any dental impression and
   designing, responsive to the capturing, a restoration based on the final implant location, such that a need for taking any dental impression having the final implant location for said designing is eliminated.

2. The method according to claim 1, wherein said overlay is done through a display.

3. The method according to claim 1, wherein the one or more preoperative images include X-ray scan data, intra-oral scan data and/or facial scan data.

4. The method according to claim 3, wherein the one or more preoperative images includes said intra-oral scan data and said designing is based on the intra-oral scan data and said final implant location.

5. The method according to claim 1, wherein the geometric registration is autonomous.

6. The method according to claim 1, wherein the common features reference points include predetermined markers, bite plane and/or dental anatomical features.

7. The method according to claim 1, wherein the treatment plan has information about the planned implant location which includes an optimal bore hole for the implant.

8. The method according to claim 1, wherein the navigational instructions are in visual, auditory and/or haptic forms.

9. A system utilizing augmented visualization, the system comprising:
   at least one processor configured to;
      obtain one or more preoperative images of a patient;
      geometrically register, responsive to the one or more preoperative images being a plurality of preoperative images, the plurality of preoperative images together based on common features or reference points in the plurality of preoperative images;
      provide a treatment plan including a planned implant location;
      overlay the (i) one preoperative image or geometrically registered preoperative images and the (ii) planned implant location on the patient such that they appear directly superimposed on target regions of the patient, to define a positional relationship between the one preoperative image or geometrically registered preoperative images and the planned implant location; and
      continuously update, using a tracking device, the overlaid one preoperative image or geometrically registered preoperative images and the planned implant location in real time such that they appear directly superimposed on said target regions of the patient:
      provide navigational instructions for creating a drilling hole based said on (a) positional relationship and (b) data tracking a clinical environment of the patient, data tracking a handpiece location relative to the clinical environment of the patient and data tracking movements of the drill based on drill geometry data; and
      provide navigational instructions for, responsive to creating the drilling hole, placing an implant into said drilling hole based on (a) said positional relationship and (c) data tracking a clinical environment of the patient, data tracking a handpiece location relative to the clinical environment of the patient and data tracking movements of an implant driver based on driver geometry data
   wherein the processor is further configured to:
   determine, responsive to placing the implant into said drilling hole, a final implant location, by capturing geometric information about the placed implant, based on d) a geometry data of the handpiece components of the handpiece and/or implant said capturing being devoid of any dental impression and
   design, responsive to the capturing, a restoration based on the final implant location, such that a need for taking any dental impression having the final implant location for said designing is eliminated.

10. The system according to claim 9 further comprising a display device configured to receive images for said overlay.

11. The system according to claim 9, wherein the tracking device is configured to offer real-time position data for a precise location and orientation of images and objects in a common coordinate system.

12. The system according to claim 11, wherein the tracking device is sensor based and/or vision based.

13. The system according to claim 9, wherein the one or more preoperative images include X-ray scan data, intra-oral scan data and/or facial scan data.

14. The system according to claim 9, wherein the geometric registration is autonomous.

15. The system according to claim 9, wherein the common features or, reference points include predetermined markers, bite plane and/or dental anatomical features.

16. The system according to claim 9, wherein the treatment plan has information about the planned implant location which includes an optimal bore hole for the implant.

17. The system according to claim 9, wherein the processor is further configured to provide the navigational instructions in visual, auditory and/or haptic forms.

18. A method comprising:
   obtaining one or more preoperative images of a patient;
   responsive to the one or more preoperative images being a plurality of preoperative images, geometrically registering the plurality of preoperative images together based on common features or reference points in the plurality of preoperative images;
   providing a treatment plan including a planned implant location;
   overlaying the (i) one preoperative image or geometrically registered preoperative images and the (ii) planned implant location on the patient such that they appear directly superimposed on target regions of the patient, the overlaying defining a positional relationship between the one preoperative image or geometrically, registered preoperative images and the planned implant location;
   continuously updating, using a tracking device, the overlaid one preoperative image or geometrically registered preoperative images and the planned implant location in real time such that they appear directly superimposed on said target regions of the patient:
   providing navigational instructions for creating a drilling hole and for placing, using a handpiece, an implant into said drilling hole;
   determining a final implant location, by capturing geometric information about the placed implant based on geometry data of (a) the handpiece, (b) components of the handpiece and (c) implant and
   designing, responsive to the capturing, a restoration based on the final implant location and a preoperative intra-oral scan taken before placing the implant;
   wherein said geometry data includes at least a length of an implant driver used to drive the implant and a location of the handpiece relative to the clinical environment.

* * * * *